(12) United States Patent
Frisbee et al.

(10) Patent No.: US 6,391,338 B1
(45) Date of Patent: *May 21, 2002

(54) SYSTEM FOR RENDERING SUBSTANTIALLY NON-DISSOLUBLE BIO-AFFECTING AGENTS BIO-AVAILABLE

(75) Inventors: Steven E. Frisbee, Reston, VA (US); Garry L. Myers, Kingsport, TN (US); Richard C. Fuisz, McLean; Andrea S. Blake, Chantilly, both of VA (US); Robert K. Yang, Flushing, NY (US)

(73) Assignee: Biovail Technologies Ltd., Chantilly, VA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/138,194

(22) Filed: Aug. 21, 1998

Related U.S. Application Data (63) Continuation-in-part of application No. 08/709,644, filed on Sep. 9, 1996, now abandoned, which is a continuation-in-part of application No. 08/524,531, filed on Sep. 7, 1995, now abandoned.

(51) Int. Cl.$^7$ .............................. A61K 9/26; A61K 9/50; A61K 9/52
(52) U.S. Cl. ..................... 424/487; 424/469; 424/497; 424/501; 427/213.36; 514/965
(58) Field of Search .......................... 427/2.21, 213.36; 424/487, 497, 501, 469; 514/965

(56) References Cited

U.S. PATENT DOCUMENTS

| | | | |
|---|---|---|---|
| 3,829,564 A | * 8/1974 | Merry et al. ................ | 424/497 |
| 4,107,288 A | 8/1978 | Oppenheim et al. .... | 424/489 X |
| 4,230,687 A | * 10/1980 | Sair et al. ................ | 424/486 X |
| 4,540,602 A | 9/1985 | Motoyama et al. .... | 427/213.31 |
| 4,855,326 A | 8/1989 | Fuisz ......................... | 514/777 |
| 4,873,085 A | 10/1989 | Fuisz ......................... | 424/400 |
| 4,997,856 A | 3/1991 | Fuisz ......................... | 514/777 |
| 5,028,632 A | 7/1991 | Fuisz ......................... | 514/772 |
| 5,034,421 A | 7/1991 | Fuisz ......................... | 514/772 |
| 5,049,322 A | * 9/1991 | Devissaguet et al. ... | 424/497 X |
| 5,118,528 A | 6/1992 | Fessi et al. ............. | 427/213.36 |
| 5,133,908 A | 7/1992 | Stainmesse et al. ......... | 264/4.1 |
| 5,145,684 A | * 9/1992 | Liversidge et al. ......... | 424/489 |
| 5,169,640 A | * 12/1992 | France et al. ........... | 424/469 X |
| 5,286,494 A | * 2/1994 | Fechner et al. ......... | 424/497 X |
| 5,380,473 A | 1/1995 | Bogue et al. .................. | 264/11 |
| 5,399,363 A | 3/1995 | Liversidge et al. ......... | 424/490 |
| 5,510,118 A | 4/1996 | Bosch et al. ................. | 424/489 |

FOREIGN PATENT DOCUMENTS

| | | | |
|---|---|---|---|
| WO | WO 95/34293 | 12/1995 | ............ A61K/9/20 |

OTHER PUBLICATIONS

Martindale—The Extra Pharmacopoeia, 30$^{th}$ Edition, Edited by J.E.F. Reynolds, The Pharmaceutical Press, London, pp. 323–326, 1993.*

BASF Pharma "Melt Extrusion: Shaping the future in Pharmaceuticals" Apr., 1996 (9 pages).

* cited by examiner

*Primary Examiner*—Richard D. Lovering
(74) *Attorney, Agent, or Firm*—Pillsbury Winthrop LLP (57) ABSTRACT

The present invention is a method of preparing a system for delivering a bio-affecting agent and the composition prepared thereby. The invention includes forming a molecular dispersion of the bio-affecting agent in an increased energy state in a water-soluble polymer which is compatible with the bio-affecting agent. As a consequence of transforming the bio-affecting agent to an increased-energy condition and freezing it in such condition in a water-soluble polymer, the bio-affecting agent is made available ("bio-available") to a bio-system upon dissolution of the polymer. This method and composition has been found extremely effective for delivery of otherwise substantially non-soluble drugs and other bio-affecting ingredients.

22 Claims, 4 Drawing Sheets

SYSTEM FOR RENDERING SUBSTANTIALLY NON-DISSOLUBLE BIO-AFFECTING AGENTS BIO-AVAILABLE

This application is a continuation-in-part of Ser. No. 08/709,644, filed Sep. 9, 1996, now Abandoned which was a continuation-in-part of application Ser. No. 08/524,531, filed on Sep. 7, 1995, now Abandoned the entire disclosures of which are incorporated herein by reference.

BACKGROUND OF THE INVENTION

The present invention relates to the art of administering bio-affecting agents to bio-systems, and, in particular, for rendering agents, which are substantially non-dissoluble in an aqueous environment, available for interaction with a host bio-system, e.g., a human or animal.

Bio-systems, such as humans, plants, insects, fish, birds, and mammals, are primarily aqueous systems. In order to effectively administer an bio-affecting agent to such bio-systems, it is necessary to make the agent available for interaction with physiological activity in the bio-system. This is referred to herein as "bio-availability." In the case of bio-affecting agents which are non-dissoluble in an aqueous environment, as well as in the case of those which are only poorly water-soluble, effective administration of the bio-affecting agent can be difficult due to inadequate bio-availability of the agent and consequent low pharmacological activity. These solubility problems affect many parameters of administration, such as the method of administration, the rate of administration, the concentration of administration, etc.

It is known that rate of dissolution of drug particulates can be increased by increasing the surface area of the solid, i.e., decreasing the particle size. Consequently, methods of making finely divided drugs have been studied and efforts have been made to control the size and size range of drug particles in pharmaceutical compositions. For example, dry milling techniques have been used to reduce particle size and thereby influence drug absorption. However, in conventional dry milling, as discussed by Lachman et al., *The Theory and Practice of Industrial Pharmacy*, Chapter 2, "Milling", p. 45 (1986), the limit of fineness is reached in the region of about 100 $\mu$m (=100,000 nm), where the milled material begins to cake onto the surfaces of the milling chamber. Lachman et al. note that wet grinding is beneficial in further reducing particle size, but that flocculation restricts the lower particle size limit to approximately 10 $\mu$m (=10,000 nm). There tends to be a bias in the pharmaceutical art against wet milling due to concerns associated with contamination. Commercial airjet milling techniques have provided particles ranging in average particle size from as low as about 1 $\mu$m to 50 $\mu$m (=1,000 nm to 50,000 nm).

Other techniques for preparing pharmaceutical compositions with enhanced aqueous solubility properties include loading drugs into liposomes or polymers, e.g., during emulsion polymerization. However, such techniques have problems and limitations. For example, a lipid-soluble drug is often required in preparing suitable liposomes. Further, unacceptably large amounts of the liposome or polymer are often required to prepare unit drug doses. Further still, techniques for preparing such pharmaceutical compositions tend to be complex. A principal technical difficulty encountered with emulsion polymerization is the removal of contaminants, such as unreacted monomer or initiator (which can be toxic) at the end of the manufacturing process.

U.S. Pat. No. 4,540,602 (Motoyama et al.) discloses a solid drug pulverized in an aqueous solution of a water-soluble high molecular weight substance using a wet grinding machine. However, Motoyama et al. teach that, as a result of such wet grinding, the drug is formed into finely divided particles ranging from 0.5 $\mu$m (500 nm) to less than 5 $\mu$m (5,000 nm) in diameter.

EPO 275,796 describes the production of colloidally dispersible systems comprising a substance in the form of spherical particles smaller than 500 nm. However, the method involves a precipitation effected by mixing a solution of the substance and a miscible non-solvent for the substance, and results in the formation of non-crystalline nanoparticles. Furthermore, precipitation techniques for preparing particles tend to provide particles contaminated with solvents. Such solvents are often toxic and can be very difficult, if not impossible, to adequately remove to pharmaceutically acceptable levels. Accordingly precipitation methods are usually impractical.

U.S. Pat. No. 4,107,288 describes particles in the size range from 10 to 1,000 nm containing a biologically or pharmacodynamically active material. However, the particles comprise a crosslinked matrix of macromolecules having the active material supported on or incorporated into the matrix.

U.S. Pat. No. 5,145,684 describes a method for providing drug particles having an effective average particle size of less than about 400 nm. The method includes wet milling the drug in the presence of a grinding medium in conjunction with a surface modifier. As in previous methods, the '684 protocol requires grinding or milling to produce size reduction. The method further requires the use of an additive in the form of a surface modifier.

Moreover, drugs prepared by milling, even wet milling such as that described in the '684 disclosure, are subject to degradation resulting from heat as well as physical and chemical trauma associated with fracture. Grinding also creates "hot spots," i.e., volumes of localized higher temperatures which can exceed the melting point or degradation of the drug. The process is also lengthy, requiring attrition exposure over several days. This type of process effectively exposes the drug to a long "heat history", wherein exposure to elevated temperatures has been significant, and the purity and potency of the drug is diminished to a significant extent. Furthermore, particles reduced by milling are often contaminated by the residue of the grinding operations, especially when ball milling is used and the grinding balls are worn down by abrasion.

It has also been known in the art of drug delivery to improve bio-availability by aggregating substantially non-dissoluble active ingredients on the surface of soluble substrates, such as water-soluble beads. The active ingredient can be deposited on such substrates by spraying a solution of the active ingredient over a fluidized bed while "flashing off" the solvent used for the active ingredient. This method is highly inefficient in that it requires several hours to deposit a sufficient amount of active ingredient to prepare a useable delivery system. Furthermore, an additional ingredient which is unnecessary to the system must be used, i.e., the solvent required to dissolve the active ingredient. As previously mentioned, the solvent must be flashed off during aggregation. Thus, this system is a long and cumbersome process and does not provide efficiency of dosage delivery.

Solubilization techniques for drugs which have low aqueous solubility require the use of organic solvents for processing in a solution state. This requires the use of expensive recovery systems for solvent handling capability. When general melt processing techniques are used to form dispersions, bulk melting and mixing steps often expose the drug to a prolonged heat history.

It is desirable to provide stable dispersible drug particles in the sub-micrometer size range which can be readily prepared in the absence of size reduction by grinding or milling. Moreover, it would be highly desirable to provide pharmaceutical compositions having enhanced bio-availability.

It is, therefore, an object of the present invention to overcome the disadvantages associated with methods for preparing delivery systems for bio-affecting ingredients, especially those which are substantially non-dissoluble. As a consequence of overcoming the drawbacks known in the art, it has been found that other and further objects which enhance the art of delivery systems have been realized as a result of the present invention.

SUMMARY OF THE INVENTION

The invention is a composition for delivery of a bio-affecting agent to a bio-system, and a methods of making and using a delivery system which includes a bio-affecting agent. The composition and method include the use of:

a solid dispersion of the bio-affecting agent in an increased-energy state in a water-soluble (or water-dispersible) polymer which is compatible with the agent and which has a glass transition temperature ($T_g$) in the range of from about 0° C. to about 200° C., whereby the agent is rendered bio-available in an aqueous environment.

Preferably, the water-soluble polymer is any polymer which has a glass transition temperature in the range of from about 25° C. to about 150° C., and more preferably in the range of from about 40° C. to about 100° C.

Preferred water-soluble polymers include poly(meth) acrylic acid polymers,containing acrylic and/or methacrylic moities. Preferably, the polymethacrylic acid polymers have the structure:

(1)

wherein: $R^1$, $R^2$, $R^3$, $R^4$ are any substituents provided that the polymer has a glass transition temperature in desired range. Accordingly, $R^1$, $R^2$, $R^3$, $R^4$ preferably are independently hydrogen (H) or any alkyl, aryl, alkaryl, aralkyl, aminoalkyl, alkyl-substituted aminoalkyl, ammonioalkyl, or alkyl-substituted ammonioalkyl group. Still more preferably, $R^1$, $R^2$, $R^3$, $R^4$ in Structure (1) are independently H, $C_1$–$C_6$ alkyl, aminoalkyl, methyl- or dimethyl-aminoalkyl, or methyl-, dimethyl-, or trimethyl-ammonioalkyl. Yet more preferably, in Structure (1):

$R^1$ is H, $CH_3$;

$R^2$ is H, $CH_3$, $C_2H_5$, $CH_2CH_2N(CH_3)_2$;

$R^3$ is H, $CH_3$; and $R^4$ is $CH_3$, $C_2H_5$, $C_3H_7$, $C_4H_9$, $CH_2CH_2N(CH_3)_3{}^+X-$, wherein $X^-$ is any monovalent anion.

A highly preferred water-soluble polymer is a terpolymer of butyl (meth)acrylate, (2-dimethyl aminoethyl) (meth) acrylate, and methyl (meth)acrylate in relative proportions 1:2:1.

Preferably, the water-soluble polymer is a polymer having pH-sensitive solubility in aqueous media. The water-soluble polymers preferentially have solubility in aqueous media having a pH of from about 1 to about 11. More preferably, the water-soluble polymer has solubility in acidic aqueous media, i.e., having a pH of about 7 or less.

The bio-affecting agent can be any agent known to have an effect in a biological system. Preferably, the bio-affecting agent is substantially non-dissoluble in an aqueous environment. More preferably, the bio-affecting agent has a solubility which is defined as practically insoluble or insoluble according to the USP. The bio-affecting agent is preferably selected from the group consisting of antifungals, anti-inflammatories, anti-hypertensives, antimicrobials, steroidal drugs, hormones, prostaglandins, interferons, and mixtures thereof.

Moreover, the composition comprising the bio-affecting agent and the water-soluble polymer preferably meets or exceeds USP dissolution standards for the agent.

The composition of this embodiment can include a solid dispersion provided by flash-flow processing a feedstock including the bio-affecting agent and the polymer. The flash-flow processing can be flash heat processing or flash shear processing. The flash heat processing method is particularly preferred when processing bio-affecting agents which are heat-sensitive. Alternatively, the solid dispersion can be provided by extrusion mixing for a time sufficient to form the solid dispersion. Preferably, the time of extrusion mixing is less than about 2 minutes, more preferably, less than about 30 seconds. When the solid dispersion is provided by extrusion mixing, it is highly preferred that the bio-affecting agent is an antifungal, anti-inflammatory, or anti-hypertensive agent.

The composition of the invention includes the bio-affecting agent in an at least substantially uniform or amorphous solid dispersion. Preferably, the bio-affecting agent is present in the form of nanoparticles distributed throughout the solid dispersion. More preferably, the nanoparticles have an average particle size of less than about 1,000 nm. Still more preferably, the average particle size of the nanoparticles is less than about 400 nm. The bio-affecting agent can be dispersed in the water-soluble polymer at the molecular level.

The composition can be prepared as a controlled-release particulate by mechanically reducing the solid dispersion. Preferably, the particulate is part of a dosage unit, which is preferably selected from the group consisting of capsules, tablets, and rapid-dissolve tablets. Alternatively, the solid dispersion is sized and shaped for fixation in an intravascular (or other parenteral) delivery apparatus. Moreover, the solid dispersion can be provided in the form of a slow dissolving structures such as a suppository or a lozenge or the like.

The method includes simultaneously transforming the bio-affecting agent to an increased-energy state and fixing the agent in that state. The method can include simultaneously transforming and fixing by flash-flow processing. This method includes use of flash heat processing or flash shear processing. Heat-sensitive agents are beneficially processed by flash heat processing. Alternatively, the simultaneous transforming and fixing can be effected by extrusion mixing for a time sufficient to form the solid dispersion, preferably for a time of less than about 2 minutes, more preferably less than about 30 seconds. In the latter approach, the bio-affecting agent is most preferably an antifungal, anti-inflammatory, or anti-hypertensive agent.

The method of transforming the bio-affecting agent into the increased-energy state can include reducing, in the absence of mechanical attrition, the bio-affecting agent to dispersed nanoparticles having an average particle size of less than about 1,000 nm. More preferably, the mechanical reducing yields an average particle size of the nanoparticles of less than about 400 nm. Alternatively, the method can be used to disperse the bio-affecting agent at a molecular level to provide a solid solution.

The method can further include mechanically reducing the solid dispersion to particulates. Thus, the method can further include incorporating the particulates in a dosage unit, such as a capsule or a rapid-dissolve tablet. Alternatively, the method can further include sizing and shaping the solid dispersion for fixation in an intravenous (or other parenteral) fluid delivery device. Lozenges, suppositories, and other slow release delivery structures can also be employed to deliver the bio-affecting agent.

The invention further includes method and composition for delivery of a bio-affecting agent. The composition produced by the method includes:

a) a carrier comprising a water-soluble polymer having a glass transition temperature in the range of from about 0° C. to about 200° C.; and b) a bio-affecting agent microscopically dispersed in said water-soluble polymer.

Preferably, the water-soluble polymer has pH-sensitive solubility in aqueous media. In particular, it is preferred that the water-soluble polymer be substantially indissoluble in saliva but soluble in gastric fluid.

The invention is also a method for delivering a composition of a bio-affecting agent, as described, to a bio-system. The method includes administering to the bio-system a solid dispersion comprising the bio-affecting agent fixed in an increased-energy state in a water-soluble polymer having a glass transition temperature in the range of from about 0° C. to about 200° C., wherein the solid dispersion renders the bio-affecting agent bio-available to the bio-system.

The method and composition of the invention possess numerous advantages over the prior art. For example, the method of processing a bio-affecting agent with a water-soluble polymer to form a solid dispersion according to the invention avoids use of solvents or mechanical attrition or comminution, which methods have various disadvantages detailed hereinabove. Moreover, the method substantially decreases the heat history of the bio-affecting agent, with the advantage that the agent remains substantially less degraded or decomposed throughout the processing. The method and composition of the invention also dramatically enhance the bio-availability of bio-affecting agents which are otherwise substantially non-dissoluble in aqueous environments, thereby enabling delivery of such agents to bio-systems with greater ease and simplicity and through more routes than has heretofore been possible.

These and further advantages will be appreciated by those skilled in the art in view of the following detailed description of the invention and the drawings as set forth below, and the scope of the invention will be pointed out in the appended claims.

BRIEF DESCRIPTION OF THE DRAWINGS

FIG. 1 is a graph which shows the effectiveness of the present invention by depicting the profile of the dissolution characteristics of a solid dispersion prepared by flash heat processing according to the present invention.

FIG. 2 is a graph showing the dissolution profile of bulk nifedipine which has not been prepared for enhanced dissolution.

FIG. 3 is a graph which shows the effectiveness of the present invention by depicting the profile of the dissolution characteristics of a solid dispersion of nifedipine prepared by extrusion processing according to the present invention.

FIG. 4 is a graph which shows the effectiveness of the present invention by depicting the profile of the dissolution characteristics of the present invention as compared to a known delivery system for itraconazole and as compared to dissolution of bulk drug substance which has not been prepared for enhanced dissolution.

DETAILED DESCRIPTION OF THE INVENTION

The present invention is a composition and method of preparing a composition for delivering a bio-affecting agent and rendering the bio-affecting agent bio-available in an aqueous environment. The composition of the present invention can be referred to as a solid dispersion of the bio-affecting agent in a water-soluble polymer.

The present invention is both a composition and method for delivery of a bio-affecting agent to a substantially aqueous bio-environment. The present invention renders the bio-affecting agent more bio-available in the aqueous environment. The method for preparing the unique composition of the present invention includes 1) transforming the bio-affecting agent to an "increased-energy" state, and 2) fixing the bio-affecting agent in the "increased-energy" state in a water-soluble polymer. The terms "increased-energy" or "higher energy" state refer to the stable dispersion of a bio-affecting agent or drug in a solid matrix, such that the bio-affecting agent is either dispersed at a molecular level or is dispersed in microscopic particulate domains having an average particle size of less than 1000 nm, and preferably less than about 400 nm. The increased energy state is achieved by modifying particle formation rather than by size reduction through grinding or attrition. Generally, the invention transforms the bio-affecting agent into solution form or nanoparticle form which has a higher surface energy or free energy than, for example, native crystals which can have an average size of over 10 μm.

The composition of the present invention is described herein as being preferably a molecular dispersion of the bio-affecting agent in the water-soluble polymer. Upon dissolution of the polymer in the bio-system, the bio-affecting agent is rendered bio-available to the host. "Bio-availability" as used herein means that the bio-affecting agent is taken up by the host bio-system for interaction with the bio-affecting agent. The mechanism for being "taken up" includes, but is not limited to, absorption, adsorption, transference, cohesion, adhesion, chemical, biological, and biochemical reactions, etc.

The invention improves the bio-availability of bio-affecting agents, especially those whose activity is otherwise limited or eliminated because of their relative inability to be dissolved into aqueous media. The term "substantially non-dissoluble" is applied to materials which are either substantially insoluble in water or are not water-soluble to any appreciable degree. Thus, substantially non-dissoluble bio-affecting agents include those bio-affecting agents which are either non-soluble or only sparingly soluble in biological fluids, such as blood, lymph, gastrointestinal fluids, cerebrospinal fluid, plant saps, and the like. The bio-affecting agents typically are not enterosoluble as defined hereinbelow.

A material may be said to be "substantially non-dissoluble" if it has a solubility of less than 10 mg/mL in water (or other aqueous medium) having a pH of from about 1 to about 8. The solubility of any substance in an aqueous medium is a property which is readily determined by a skilled artisan. In fact, the solubilities of many substances, including drugs, are known and published in compendia such as *The Merck Index,* 12th edition (1996). Most preferably, the bio-affecting agent has a solubility low enough to qualify the agent as "practically insoluble, or insoluble" as defined by the USP. According to this definition, the bio-affecting agent is substantially non-dissoluble if it has a solubility requiring at least 10,000 parts of solvent (aqueous medium) for 1 part of the solute (bio-affecting agent).

It is believed that all bio-affecting agents can be used in the present invention, but the invention is particularly directed to combining a substantially non-dissoluble bio-affecting agent with a water-soluble polymer in a unique manner to render the non-dissoluble agent bio-available. Substances which would otherwise be capable of being bio-affecting as defined herein, but which qualify as substantially non-dissoluble, are preferred for delivery according to the invention. It is also contemplated that a substantially non-dissoluble bio-affecting agent can be used in combination with other substances, including other bio-affecting agents, which are substantially more soluble in aqueous media.

The polymers which are useful as "water-soluble polymers" in the present invention include polymers, copolymers, terpolymers, interpolymers, polymeric amalgams, etc., having molecular weights which range from oligomers to high molecular weight polymeric substances and polymers having pH dependent solubility characteristics. "Water-soluble," as used herein, applies to polymers which readily dissolve or disperse in water and other aqueous media at any or all pH values without the assistance of a dissolution-promoting substances such as surfactants, emulsifiers, etc. The fact that the polymer does not require an agent to mediate its dissolution in an aqueous environment does not mean, however, that delivery systems prepared in accordance with the present invention do not include such agents. In order to engineer the appropriate delivery system, any additional substances which are required to control, promote, mediate, or modulate the bio-availability of the bio-affecting agent(s) can be used. These substances are referred to herein as "bio-availability promoters." Furthermore, combinations of bio-availability promoters can be used in the present delivery systems.

By virtue of the present invention the bio-availability of a bio-affecting agent is enhanced by altering the physico-chemical condition of the bio-affecting agent. This is achieved by processing the bio-affecting agent with a water-soluble polymeric carrier to produce a solid dispersion of the bio-affecting agent in the polymer. By "solid dispersion" is meant an apparently homogeneous solid substance which consists of a microscopically heterogenous mixture of the bio-affecting agent and the water-soluble polymer (and other materials as otherwise defined herein). In conventional terminology, the bio-affecting agent constitutes the "dispersed phase", while the water-soluble polymer constitutes the "dispersion medium" or "continuous phase."

The method(s) of the present invention can be used to make solid dispersion compositions which are either:

a) Solution systems where at least a portion, and preferably all of the bio-affecting agent is in solution phase with the polymer or dispersed at the molecular level (i.e., "molecular dispersions"); or b) Heterogenous systems where the bio-affecting agent is present in more or less discrete supramolecular domains (nanoparticles), which may be aggregates of molecules, uniformly dispersed within the polymer. Furthermore, as a result of the quenching of the water-soluble polymer in accordance with the present invention, the bio-affecting agent is prevented from forming macro-scale distinct phases or large domains in the final product.

By "molecular dispersions" applicants mean solid solutions wherein all or a portion of the bio-affecting agent(s) is in solution phase in the polymer(s) or is dispersed at a molecular level therein.

As noted, the solid dispersion can include discrete domains of the bio-affecting substance distributed substantially homogeneously throughout the polymeric medium. When present, these discrete domains are generally referred to herein as "nanoparticles." In the case of crystallizable bio-affecting agents, the domains of the bio-affecting agent might be designated "nanocrystals." These terms connote the extraordinarily small dimensionality of the dispersed phase of the solid dispersions of the invention. Specifically, the particles of dispersed phase in the solid dispersions are typically of the order of nanometers ($\sim 1\times 10^{-9}$ m) to hundreds of nanometers ($\sim 100\times 10^{-9}$ m). Thus, the scale of such particles is conveniently referred to as "nanometer-scale" or "nanoscale." It is believed that this feature of the processing method of the invention significantly contributes to increasing the bio-availability of the bio-affecting agent.

Other solid dispersions according to the invention include the bio-affecting agent dispersed at the molecular level through the water-soluble polymer. These solid dispersions of the invention may be characterized as solid solutions, since they meet the criteria conventionally reserved for solutions. Typically, little or no supramolecular organization is present in such solutions. However, it must be recognized that a solid dispersion according to the invention can include the bio-affecting agent in a range of physical states ranging from molecular dispersion to amorphous or pre-crystalline associations of molecules to nanoparticulate domains.

The solid dispersions of the invention, therefore, refer to intimate mixtures of two or more components which form a continuum wherein substantially all domains of the bio-affecting agent have a higher entropy than the entropy of the agent in its native condition. As a result of forming the solid dispersions of the present invention, the bio-affecting agent is fixed or frozen in the solid water-soluble polymer in an increased-energy state. "Increased-energy state" as used herein means a physicochemical condition of the bio-affecting agent which has a higher entropy than the bio-affecting agent would have in its native condition. For example, the bio-affecting agent is, in a preferred embodiment, converted to a substantially amorphous form and dispersed throughout the water-soluble polymer in the melt condition such that, when the agent crystallizes (if, in fact, it does crystallize), the average crystal size will constitute particles of nanoscale dimension, i.e., nanoparticles. The bio-affecting agent is thereby captured in a highly randomized condition as compared to the bio-affecting agent in its native form. The increased energy state of the present invention is sufficient to render the drug more bio-available in an aqueous environment. As previously discussed herein, bio-available means a condition which permits the active ingredient to interact with, i.e., become available for use in, the target bio-system, i.e., the body of the host animal or human patient.

The composition of the present invention, referred to herein as a molecular dispersion, can be formed by a number of techniques. In one preferred embodiment the molecular dispersion is formed by subjecting a feedstock which includes both the agent and the polymer to flash-flow processing. Flash-flow processing is defined hereinbelow and includes both flash-heat processing and flash-shear processing. Alternatively, it has been found that the molecular dispersion of the present invention can be provided by extrusion mixing the agent and the polymer for a time sufficient to transform and fix the agent during quenching. In a preferred embodiment, the time required to extrusion mix the ingredients is less than about two minutes (2 min), and is preferably less than about thirty seconds (30 sec).

As a result of the present invention, the bio-affecting agent can be provided as a solid dosage form which has an enhanced dissolution rate which can often be simulated by in vitro data. It is theorized that the increases in dissolution rate are achieved by a combination of effects, the most significant being the reduction of particle size to an extent not achieved by conventional comminution approaches. The smaller size particle (i.e., the nanoparticles of the invention) apparently imparts to the bio-affecting agent a higher surface energy or free energy than the agent has in its original or native state, providing for enhanced solubility in water, generally corresponding to enhanced bio-availability in the bio-system. As previously mentioned, techniques known to date for producing dispersions in the prior art generally require either the solubilization or melting of a drug with a freely soluble carrier in a water-like (low viscosity) state, followed by further processing to precipitate or congeal the material into a solid form.

The technique and composition of the present invention has inherent advantages in the production of solid dispersions of bio-affecting agents. As a result of the present invention, the bio-affecting agent and the carrier polymer can be combined in a process which mixes, melts, forms, and solidifies in a continuous process, to provide the bio-affecting agent in a solid solution or dispersion and having an increased energy condition as defined hereinabove. The resulting compositions are easily employed to make any of a variety of delivery systems, including tablets, etc., which would otherwise be incapable of effectively delivering the bio-affecting agent.

Another very important advantage of the invention is that the bio-affecting agent is exposed to a lower heat history during the process of being rendered bio-available. The heat history required in the inventive process is very short compared to conventional techniques used in the formation of congealed materials. Consequently, the process of the invention induces less degradation or decomposition of the bio-affecting agent, meaning that purity and potency are improved over prior art systems. This is particularly beneficial for those bio-affecting agents which are heat-sensitive.

The systems of the present invention are implemented by the use of bio-affecting agents and water-soluble polymers which are "compatible" with each other. The term "compatible" is used herein to mean that the polymer has physical characteristics which render it processable according to the invention. Specifically, the water-soluble polymer must be capable of being processed at temperatures at or above the melting point ($T_m$) of the bio-affecting agent but below the temperature of decomposition ($T_d$) of the bio-affecting agent and the polymer. Consequently, it is preferable to use a polymer which is flowable (generally, thermoplastic) at a temperature which is equal to or above the melting point of the bio-affecting agent, but below the decomposition temperature of either the agent or the polymer itself.

Moreover, bio-affecting agents and polymers are said to be "compatible" if they are soluble or dispersible in each other in the flowable/non-decomposition stage. For example, if one were to visualize the bio-affecting agent/water-soluble polymer composition immediately after solidification, in many cases it would appear substantially as a transparent or translucent glass, i.e., any inhomogeneities are of a scale such that one cannot visually distinguish the solubilized bio-affecting agent from the water-soluble polymer.

Compatibility herein also means that the polymer and bio-affecting agent solidify such that the bio-affecting agent is captured in an "increased-energy" condition and held stably in that state following completion of solidification. The bio-affecting agents may later crystallize, but any crystals which form are of the order of nanoparticles, i.e., the crystals will have a condition of considerably higher entropy than the native crystals of the agent, which have an average particle size generally in the range of from about 10 μm to about 50 μm. If the polymer and bio-affecting agent solidify at rates which permit the bio-affecting agent to form domains which essentially return the bio-affecting agent to a lower entropy form, e.g., a crystal size which approximates the agent in its native condition, then the combination is not considered compatible as defined herein. More importantly, little or no improvement in bio-availability is obtained by such incompatible combinations. Thus, compatibility further means that the polymer is capable of being quenched or formed into a solid along with the bio-affecting agent such that the bio-affecting agent is not permitted to return to a lower energy state, or to a condition of particles having an average size of greater than about 1000 nm.

In the case of itraconazole, crystallization occurs at a later time, but the crystals are on the order of nanocrystals which is at a condition of considerably higher entropy than the native itraconazole crystals which are generally in the range of 10 to 50 microns average particle size. If the polymer and bio-affecting agent solidify at rates which permit the bio-affecting agent to form domains which essentially return the bio-affecting agent to lower entropy form, i.e., crystal size which approximates the agent in its native condition, then the combination is not considered compatible as used herein. In the case of itraconazole, it has been found that a copolymer of diethylaminoethyl methacrylate and methacrylic acid esters known as Eudragit® E100, which is marketed by Rohm GmbH, has been found to be compatible with itraconazole.

The composition of the present invention is referred to herein as a solid dispersion and can be formed in a preferred embodiment by subjecting a feedstock which includes both the agent and the polymer to flash-flow processing. Flash-flow processing is defined herein-below and includes both flash-heat processing and flash-shear processing. Alternatively, it has been found that the solid dispersion of the present composition can be provided by extrusion mixing the agent and the polymer for a time sufficient to transform and fix the agent during quenching. In a preferred embodiment, the time required to extrusion mix the ingredients is less than about two (2) minutes, and is preferably less than about thirteen (13) seconds.

It is, of course, preferred that the polymer have physical characteristics which promote the formation of solid dispersions described herein. Applicants have unexpectedly found that glass transition temperature ($T_g$) is a property of polymers which correlates well with the usefulness of polymers in the method of the invention. In particular, Applicants have found it to be preferred that the polymer has a $T_g$ in the range of from about 0° C. to about 200° C. More preferably, the polymer has a $T_g$ in the range of from about 25° C. to about 150° C. Still more preferably, the polymer has a $T_g$ in the range of from about 40 ° C. to about 100 ° C.

Applicants have found that $T_g$ is related to the flowability or processability of the polymer, with a lower $T_g$ generally correlating with a lower viscosity at a given temperature. Polymers having a $T_g$ outside of the temperature ranges set forth above are less desirable. On the one hand, if the $T_g$ is too high, the polymer will tend to be too viscous, making the polymer difficult to process. On the other hand, if the $T_g$ is too low, the polymer may not be viscous enough to effectively capture or freeze the bio-affecting agent in the desired increased-energy state. Moreover, Applicants have found that the polymers characterized by the $T_g$ ranges given above tend to have solubilities in aqueous environments sufficient to render them effective for enhancing the bio-availability of non-dissoluble bio-affecting agents.

The polymers useful according to the invention generally also meet other physicochemical characteristics. For example, the polymers useful in this invention generally have an average molecular weight of above 500 daltons (Da), and preferably above 1500 Da. Polymers having molecular weights of 100,000 Da or more may be preferred for particular applications. Also, the water-soluble polymers of the present invention preferably have an intrinsic viscosity of from about 1,000 centipoise (cP) to millions of cP, and a melt viscosity of from about 50 cP to about 100,000 cP. The viscosity of the polymer can be measured by a Brookfield Viscometer. It is also believed that polymers which do not crystallize are probably preferable to those which do crystallize, but this property is not well understood.

Polymethacrylic acid polymers (also referred to herein as "polymethacrylates") are among the water-soluble polymers preferred for use according to the invention. For example, preferred polymethacrylates have the general structure:

(1)

wherein: $R^1$, $R^2$, $R^3$, $R^4$ are independently hydrogen (H) or any alkyl, aryl, alkaryl, aralkyl, aminoalkyl, alkyl-substituted aminoalkyl, ammonioalkyl, or alkyl-substituted ammonioalkyl group.

Preferably, $R^1$, $R^2$, $R^3$, $R^4$ are independently H, $C_1$–$C_6$ alkyl, amino ($C_1$–$C_6$)-alkyl, methyl- or dimethyl-aminoalkyl, or methyl-, dimethyl-, or trimethyl-ammonioalkyl.

More preferably the polymethacrylates of Structure (1) have the following substituents:

$R^1$ is H, $CH_3$;

$R^2$ is H, $CH_3$, $C_2H_5$, $CH_2CH_2N(CH_3)_2$;

$R^3$ is H, $CH_3$; and $R^4$ is $CH_3$, $C_2H_5$, $C_3H_7$, $C_4H_9$, $CH_2CH_2N(CH_3)_3^+X^-$.

where $X^-$ is any monovalent anion, preferably $Cl^-$.

Exemplary polymethacrylic acid polymers are described in detail in A. J. Shukla, "Polymethacrylates", pp. 362–366 in *Handbook of Pharmaceutical Excipients,* 2d ed., Ainley Wade and Paul J. Weller, eds. (1994). A large number of these polymers are available as coating materials under the EUDRAGIT trade name from Röhm GmbH. One polymer found to be particularly effective is a methacrylic acid ester terpolymeric product of butyl methacrylate, (2-dimethyl aminoethyl) methacrylate, and methyl methacrylate in proportions 1:2:1, sold as EUDRAGIT E.

It is preferred that the water-soluble polymers be polymers whose solubility is pH-sensitive. Specifically, the polymer is said to be pH-sensitive if its solubility in an aqueous medium is affected by pH. Preferably, the water-soluble polymers used in the method and composition of the invention have higher solubility at pH 1 to pH 10, than at a pH outside this range. More preferred polymers are those which are substantially more soluble at acid pH than at neutral or basic pH. Thus, the water-soluble polymer is desirably soluble below pH 7. By selecting a water-soluble polymer having a pH-sensitive solubility, specifically an acid-sensitive solubility, solubility of the solid dispersions of the invention can be minimized until the material are exposed to acid conditions. Thus, materials can be manufactured which are substantially indissoluble in saliva but soluble in gastric fluid, thereby permitting selective control over the bio-availability of the bio-affecting agent. (In certain applications, namely delivering the bio-affecting agent to the intestine, the water-soluble polymer preferably has an alkali-sensitive solubility.) All such polymers are termed "entero-soluble."

Preferred enterosoluble polymers can also be defined according to the comonomers from which they are prepared. For example, the copolymers and terpolymers of methacrylic acid with methyl acrylate and/or methyl methacrylate are highly preferred, having solubilities in the range of from about pH 5.5 to about pH 7.2. Such polymers have been described for use as enteric coatings for tablet preparation. Lehmann et al., "New methacrylic acid copolymers for improved coating technology," Presentation from AAPS Tenth Annual Meeting (1995), published by Hüls America Inc.

The EUDRAGIT polymers possess solubilities which are sensitive to pH, meaning that their solubilities may be higher at certain pHs and lower at others. Depending upon pH, the solubility of these polymers can vary over an order of magnitude or more. Certain of the polymethacrylates have high aqueous solubility under acidic conditions, and have been used to promote rapid release of active agents in the gastric region of the gastrointestinal tract. The EUDRAGIT E product has such acid-sensitive solubility, being soluble in gastric fluid and weakly acidic buffer solutions (i.e., less that about pH 5). Others are preferentially soluble in mild alkali (e.g., pH 6–7) and therefore are suitable for delivering bio-affecting substances to the intestine while bypassing the gastric region. However, these polymethacrylates have not been employed as solid solution carrier materials for bio-affecting agents, a new application to which Applicants have unexpectedly found them to be very well adapted.

Preferably, the bio-affecting agents suitable for use in the method and composition of the invention are drugs which are potentially bio-affecting to animals, including humans and other mammals. A non-limiting list of these bio-affecting agents includes, for example: antitussives, antihistamines, decongestants, alkaloids, mineral supplements, laxatives, vitamins, antacids, ion exchange resins, anti-cholesterolemics, anti-lipid agents, antiarrhythmics, antipyretics, analgesics, appetite suppressants, expectorants, anti-anxiety agents, anti-ulcer agents, anti-inflammatory substances, coronary dilators, cerebral dilators, peripheral vasodilators, anti-infectives, antifungals, antivirals, psychotropics, antimanics, stimulants, gastrointestinal agents, sedatives, antidiarrheal preparations, anti-anginal drugs, vasodilators, anti-hypertensive drugs, vasoconstrictors, migraine treatments, antibiotics, tranquilizers, anti-psychotics, antitumor drugs, anticoagulants, antithrombotic drugs, hypnotics, anti-emetics, anti-nauseants, anti-convulsants, neuromuscular drugs, hyper- and hypoglycemic agents, thyroid and antithyroid preparations, diuretics, antispasmodics, uterine relaxants, mineral and nutritional additives, anti-obesity drugs, anabolic drugs, erythropoietic drugs, anti-asthmatics, cough suppressants, mucolytics, anti-uricemic drugs, prostaglandins, interferons, cytokines, steroidal and peptide hormones, proteins, and mixtures thereof.

Other bio-affecting agents for use in the present invention include antidiarrheals such as IMODIUM AD, antihistamines, antitussives, decongestants, vitamins, and breath fresheners. Also contemplated for use herein are anxiolytics such as XANAX; antipsychotics such as CLOZARIL and HALDOL; non-steroidal anti-inflammatories (NSAID's) such as VOLTAREN and LODINE; antihistamines such as SELDANE, HISMANAL, RELAFEN, and TAVIST; antiemetics such as KYTRIL and cesamet; bronchodilators such as bentolin, PROVENTIL; antidepressants such as PROZAC, ZOLOFT, and PAXIL; anti-migraines such as imigran; ACE-inhibitors such as VASOTEC, CAPOTEN and ZESTRIL; anti-Alzheimer's agents such as nicergoline; and $Ca^H$-antagonists such as PROCARDIA, ADALAT, and CALAN.

The popular $H_2$-antagonists which can be used include cimetidine, ranitidine hydrochloride, famotidine, nizatidine, ebrotidine, mifentidine, roxatidine, pisatidine and aceroxatidine.

The invention is especially useful for the following substantially non-dissoluble compounds: vasodilators such as nicergoline; anti-inflammatories, antipyretics, and analgesics such as indomethacin; antiarthritics such as diacerin; progestogens, palliative treatment compounds for breast and endometrial carcinoma, and estrus regulators such as megestrol; sedatives and hypnotics such as barbitals; analgesics, anticonvulsants such as carbamazepine; antihypertensives such as nifedipine; uricosurics such as probenecid; anti-anginals such as felodipine; antispasmodics such as fenalamide; plant fungicides such as fenarimol; and anti-helminthics such as'fendendazole.

In preferred embodiments the bio-affecting agents include antifungals, anti-inflammatories, anti-hypertensives, antimicrobials, steroidal drugs, hormones, prostaglandins, interferons, and mixtures thereof.

In preferred embodiments the boi-affecting agent is an anti fungal such as griseofulvin, the bio-affecting agent is an anti fingal such as griseofulvin, itraconazole and the like.

In the case of one preferred embodiment, it has been found that the substantially non-dissoluble bio-affecting agents ibuprofen and nifedipine are each compatible with the acid soluble polymer known as EUDRAGIT E, a copolymer based on dimethylaminoethyl methacrylate and other neutral methacrylic acid esters, and marketed by Röhm GmbH. This polymer is available in solvent free granules (EUDRAGIT E 100) and in a 12.5% solution in propan-2-ol/acetone (60:40) (EUDRAGIT E 12.5). EUDRAGIT E has high aqueous solubility especially under acidic conditions (below pH 5) and provides for rapid release of the drug in the gastric region of the gastrointestinal tract. Although the polymer is principally amorphous, microcrystalline domains of the polymer can be identified in the virgin polymer.

In a preferred embodiment, the process of the present invention can be implemented by flash-flow processing. Flash-flow processing is achieved by subjecting feedstock to simultaneous application of heat and shear sufficient to permit transformation of the morphology of the feedstock. Flash-flow processing creates a condition of internal flow which means that the feedstock material is enabled to move and separate at a sub-particle level. In this embodiment, the feedstock would include a water-soluble polymer and a substantially non-dissoluble bio-affecting agent.

Flash-flow processing can be effected by flash-heat processing or flash-shear processing. In a preferred embodiment, the present invention contemplates flash-flow processing by the flash-shear method which is described in commonly known U.S. Pat. No. 5,380,473 to Bogue et al., the contents of which is incorporated herein by reference. The process reported in the Bogue et al. '473 patent is characterized by increasing the temperature of a non-solubilized feedstock carrier to a point at which it undergoes internal-flow, followed by forcibly expelling or ejecting a stream of the feedstock and subjecting the stream to disruptive fluid shear force which separates the stream into separate masses having transformed morphology.

In an alternative embodiment to the flash-shear method, the components of the present invention can be mixed and processed in a mix extrusion method without the benefit of forming disrupted masses as in the flash-shear method. As a most preferred mode of operation of this alternative embodiment, the feedstock materials e.g., a water-soluble polymer and a substantially non-dissoluble bio-affecting agent (without solubilizing additives) are subjected to mix extrusion over a very short period of time, preferably not more than about two minutes, and most preferably not more than about thirty seconds.

Another contemplated embodiment includes processing the components in a flash-heat process which creates conditions such as those found in cotton candy machines. In this process, the feedstock is introduced to a spinner head in which it is subject to heat and shear created by centrifugal force from the spinning head. Disclosures which relate to methods and apparatus suitable for spinning substances include the following: U.S. Pat. Nos. 4,855,326; 4,873,085; 5,034,421; 4,997,856; and 5,028,632.

The U.S. patents listed above describe processing feedstock material by subjecting it to high speed spinning on spinning head in which the feedstock is also subjected to heat provided by a heating element. The change of temperature is quite large, which is believed to be occasioned by the spinning head quickly and efficiently spreading the feedstock material against the heating element circumferentially disposed around the perimeter of the spinning head. Thus, extensive surface contact of the feedstock against the heating element is provided. Nonetheless, the spinning procedure is sufficiently fast that the heat history of the bio-affecting agent is not significantly prolonged.

The processes used to combine the bio-affecting agent(s) and the polymer(s) may be batch processes or continuous processes, with continuous ones being preferred.

As previously discussed herein, carriers used in the systems of the present invention are water-soluble polymers which are compatible with the bio-affecting agents selected herein. These carriers have sufficient heat stability for flash-flow processing and can range from low molecular weight crystalline or amorphous materials to high molecular weight thermoplastic polymers. Thermoplastic polymers, while having no defined melting point, can be processed in a temperature region above its glass transition temperature, where the polymers elastomeric properties are sufficient to allow elongation and dissolution of the active ingredient therein.

The present invention includes the combination of the active ingredient with the compatible polymer (and other excipients) in a melt form to enable the active ingredient to be captured in an increased-energy condition upon quenching. Thus, the bio-affecting agent is solubilized in the substrate or polymer and does not separate into its own crystalline domains. The drug may form very fine crystals (nanoparticles) in the carrier as a result of being quenched in the increased-energy condition, such crystals having significantly enhanced dissolution and/or dispersibility. In the present invention, the carriers themselves have good aqueous solubility. As a result of the system described herein, the poorly soluble drug is liberated from the solid solution or dispersion as nanoparticles as the carrier is solubilized. It is the nanoparticulate dispersion which provides the enhanced bio-availability in vivo.

It is further contemplated that the present invention can be used to provide products from the compositions resulting herein. Delivery systems can be engineered to provide the delivery profile which renders the bio-affecting agent available at the rate and intensity required to treat the host. For example, fibers which are obtained as a result of processing in accordance with the present invention can be ground to provide small particles of drug-bearing polymer. (Note that it is not the grinding of the fibers which provides a substantially homogeneous distribution of the bio-affecting agent in the carrier. Rather, unlike the prior art, the distribution of the bio-affecting agent has been effected in the antecedent process in which the fibers were formed.) The drug-bearing particles can then be coated by techniques known in the art. For example, the particles can be coated by means of the method set forth in commonly-owned copending U.S. application Ser. No. 08/334,729 which was filed on Nov. 4, 1994, and now U.S. Pat. No. 5,567,439 entitled "Delivery of Controlled-Release Systems," the disclosure of which is incorporated herein by reference. The once-coated particles can be used as controlled-release particles for capsules.

Alternatively, the drug-bearing particles resulting from grinding product processed in accordance with the present invention can be used to make tablets, preferably rapidly dissolving tablets, according to known techniques. A preferred tableting technique is the method set forth in commonly-owned copending U.S. application Ser. No. 08/259,496, filed Jun. 14, 1994 and now abandoned, and application Ser. No. PCT/U.S.95/07194, filed Jun. 6, 1995, both entitled "Process and Apparatus for Making Rapidly-Dissolving Dosage Units and Product Therefrom," the entire disclosures of which are incorporated herein by reference.

The present invention includes both the controlled-release particles resulting from grinding the fibers produced in accordance with the present invention and capsules and rapid dissolved tablets containing the controlled-released particles. With respect to these products, it should be noted that fragile fibers bearing the bio-affecting agent are easily disrupted by application of physical stress, implying that the bio-affecting agent is exposed to minimal heat during grinding to produce reduced particle size of drug bearing polymer. This is, indeed, a vast improvement over grinding raw active ingredients which generates significant heat usually encountered in forced attrition. The heat which is generated by conventional direct grinding of drugs can be sufficient to cause recrystallization, which would work to increase the average particle size. Thus, using the fragile fibers resulting from the process of the present invention, the lowest average particle size of the bio-affecting agent can be attained for delivery to the bio-system, thereby maximizing the bio-availability of the bio-affecting agent.

Tablets produced in accordance with the present invention can be processed to provide yet further desired characteristics. For example, the tablets of the present invention can be coated with a semi-permeable membrane to achieve controlled-release of the active. Furthermore, the tablets of the present invention can be formulated to contain tablet channeling agents or dissolution agents (bio-availability promoters) to increase or control breakdown of the tablet. Typical of such bio-availability promoters are cellulosics such as hydroxyethyl cellulose, hydroxypropylmethyl cellulose, etc.

Moreover, in certain embodiments, the compositions resulting from processing in accordance with the present invention can also be ground or pulverized and subjected to further processing to make agglomerates which can be tableted. This is especially useful where additional excipients are required to be added before tableting or where the composition itself is not directly tabletable.

Yet other uses of the present invention include intravascular (e.g., intravenous, intra-arterial) delivery of drugs. It is known that substantially non-dissoluble agents must be reduced significantly in size before intravascular delivery. Indeed, some agents cannot be delivered intravascularly. As a result of the present invention, however, a mass of drug-bearing water-soluble polymer can be contacted with intravascularly fed fluid for delivery to the patient. The mass can be placed directly in the stream of flow of the fluid. Alternatively, the mass can be housed in a compartment by which the intravascular fluid passes in such a manner so that the drug is delivered by the fluid. In the embodiments in which the bio-affecting agents are used in intravascular applications, a colloid stabilizer is generally used to keep the particles of bio-affecting agents dispersed.

The composition and method of the present invention is a highly efficient system for providing a drug delivery system as a commercial product. The compositions of the invention can be used for intramuscular injection, parenteral dosage, intranasal, in osmotic pumps, erodible systems which erode to release the bio-affecting agent, inhalants, transdermal patch systems, subcutaneous injection, vaginal pessary, suppositories, powders, intravenous (IV) administration, lozenges or other oral delivery systems, and for topical applications. Especially preferred uses are those wherein the composition is exposed to a body fluid such as perspiration or internal body fluids which solubilize the polymer and release the bio-affecting agent.

The present invention has been exemplified below in examples in which co-processed compositions of substantially non-dissoluble bio-affecting agents, e.g., ibuprofen or nifedipine, have been prepared in combination with a commercially obtained water-soluble polymethacrylate polymer. The dissolution rate of orally administered drugs which have low aqueous solubility is quite slow. Low solubility is the result of a low rate of departure of drug molecules from the undispersed state. In accordance with the present invention, formulation techniques have been provided which produce solid dispersions (or solid solutions) of a bio-affecting agent. The system formed by these formulation techniques has been found to be valuable for making non-dissoluble agents bio-available to host bio-systems.

The examples set forth hereinbelow exemplify the present composition, method, and downstream products resulting therefrom. The examples have been set forth to satisfy obligations under the statute, but are not in any way intended to limit the scope of protection provided herein.

EXAMPLES

Ibuprofen is an excellent non-steroidal anti-inflammatory drug. Nifedipine is a potent antianginal and antihypertensive drug. Both of these drugs are substantially insoluble in water and other aqueous media, as defined in the USP. These two compounds were, therefore, selected as model agents to demonstrate the capability of the present invention.

It was discovered that a polymethacrylate aqueous polymer used in pharmaceutical film coating, EUDRAGIT E, was miscible with ibuprofen or nifedipine under melt flow conditions. The specific polymer used is a copolymer based on dimethylaminoethyl methacrylate and methacrylic acid esters marketed by Röhm GmbH as EUDRAGIT E. This polymer has compendial status in the USP/INF.

Example 1
Flash-Heat Process

In this example, the polymethacrylate polymer EUDRAGIT E (EUDRAGIT E 100; pellet form) obtained from Röhm GmbH, Darmstadt, Germany, was ground to a powder and sized by passing the powder through a 60 mesh screen sieve. Ibuprofen (Product Code IB1D472, grade 25) obtained from BHC HBMC Advanced Materials Group, Bishop, Tex., was added to the resulting EUDRAGIT powder and blended together to form a blend including 20 wt % ibuprofen in 80 wt % EUDRAGIT polymer.

The powder blend was processed in a 5" pharmaceutical spinning head with 36 heaters. The machine parameters included a spinning speed of 3,600 rpm, a power setting of 20.5%, and a maximum temperature of 150° C. A fine, clear, and colorless floss was produced from the flash-heat process.

Microscopic examination of the material in simulated gastric fluid (no pepsin) revealed the release of innumerable nanoparticles as the polymer solubilized. The size of the nanoparticles was not measurable by optical means, but was well below 1 µm. It is believed that the size of the nanoparticles are of the order of 100 nm to 600 nm (i.e., 0.1 µm to 0.6 µm).

One gram (1 g) of the ibuprofen-containing solid dispersion (=200 mg of ibuprofen) was added to 900 mL of 0.1 N HCl and stirred at 100 rpm for 0.5 h. Samples were taken and ibuprofen concentration was measured by HPLC UV. The solid dispersion gave an ibuprofen concentration of 0.066 µg/mL. This corresponds to an increase in solubility of over 100% compared to the solubility of the raw drug as tested by the same analytical method (0.030 µg/mL).

Example 2
Extrusion Mixing

The water-soluble polymer, EUDRAGIT E 100 was ground from pellet form to a fine powder and sized by passage through a 60 mesh sieve. The resulting sized powder was mixed with ibuprofen and blended to form a blend including 20 wt % ibuprofen in 80 wt % EUDRAGIT polymer.

The resulting powder blend was processed in an APV-Baker MP2015 twin screw extruder with multiple heater zones and fitted with a 1 cm nozzle. The temperature of each of the four heating zones was set to 100° C., and the following temperatures were recorded: Zone 1=98° C.; Zone 2=102° C.; Zone 3=100° C.; Zone 4=105° C. The speed of the twin screw was 120 rpm. The extruded product was a solid dispersion of ibuprofen in the polymethacrylate, having a continuous rod structure.

One gram (1 g) of the ibuprofen-containing solid dispersion (=200 mg of ibuprofen) was added to 900 mL of 0.1 N HCl and stirred at 100 rpm for 0.5 h. Samples were taken and ibuprofen concentration was measured by HPLC UV. The solid dispersion gave an ibuprofen concentration of 0.067 µg/mL. This corresponds to an increase in solubility of over 100% compared to the solubility of the raw drug as tested by the same analytical method (0.030 µg/mL).

Example 3
Flash- Heat Process

Once again, the water-soluble polymer, EUDRAGIT E 100, was ground from pellet size to a fine powder and sized by passing the ground powder through a 60 mesh sieve. Nifedipine (Product Code 15620, lot 55, Sanofi) obtained from InterChem Corp., Paramus, N..J. was added to the resulting EUDRAGIT powder and blended together to form a blend including 20 wt % nifedipine in 80 wt % EUDRAGIT polymer.

The powder blend was processed in a 5 " pharmaceutical spinning head with 36 heaters. The machine parameters included a spinning speed of 3,600 rpm, a power setting of 30%, and a maximum temperature of 183° C. The spun product was a solid dispersion of nifedipine in the polymethacrylate polymer, in the form of a yellowish floss.

Figure 1:
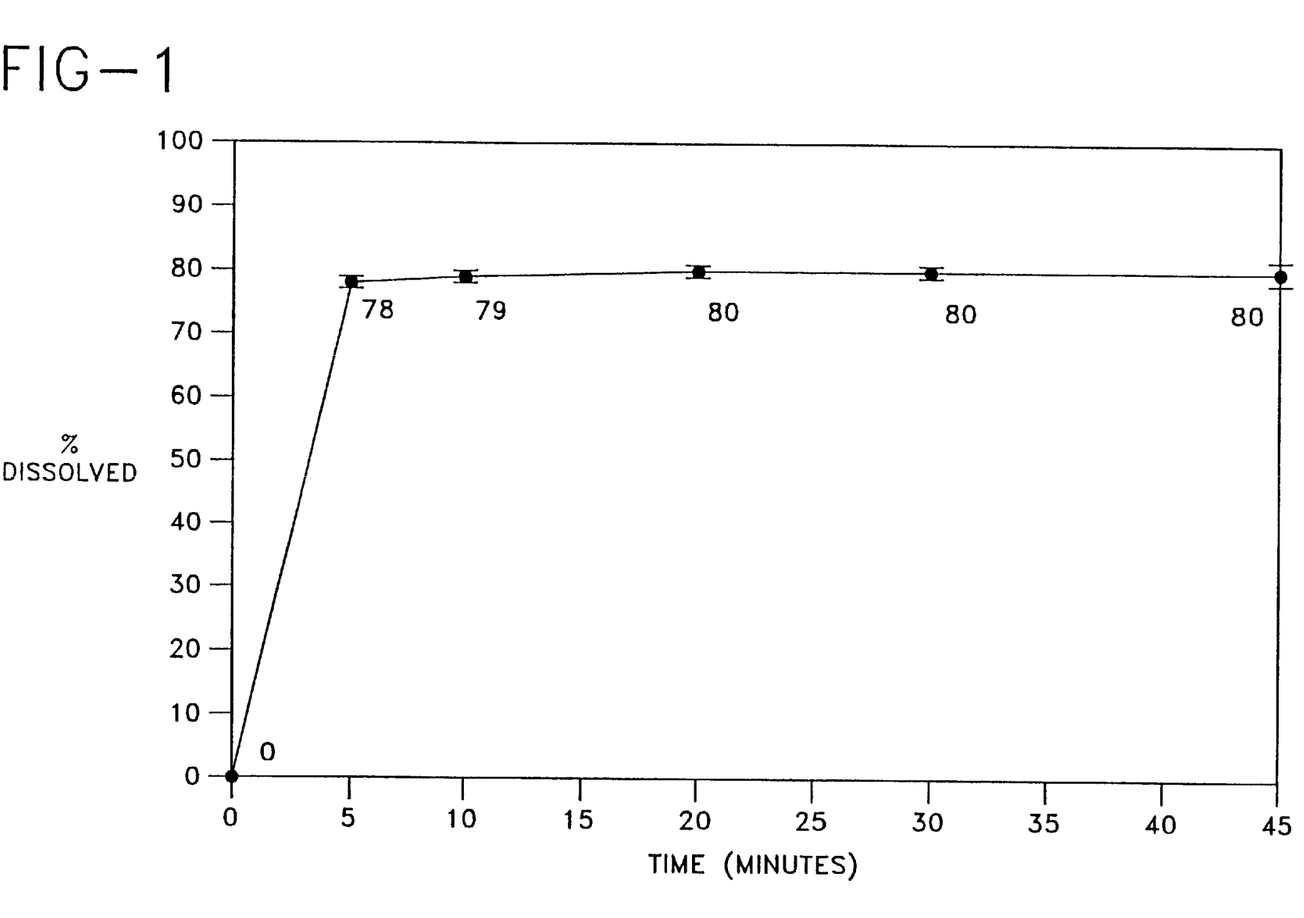
Figure 2:
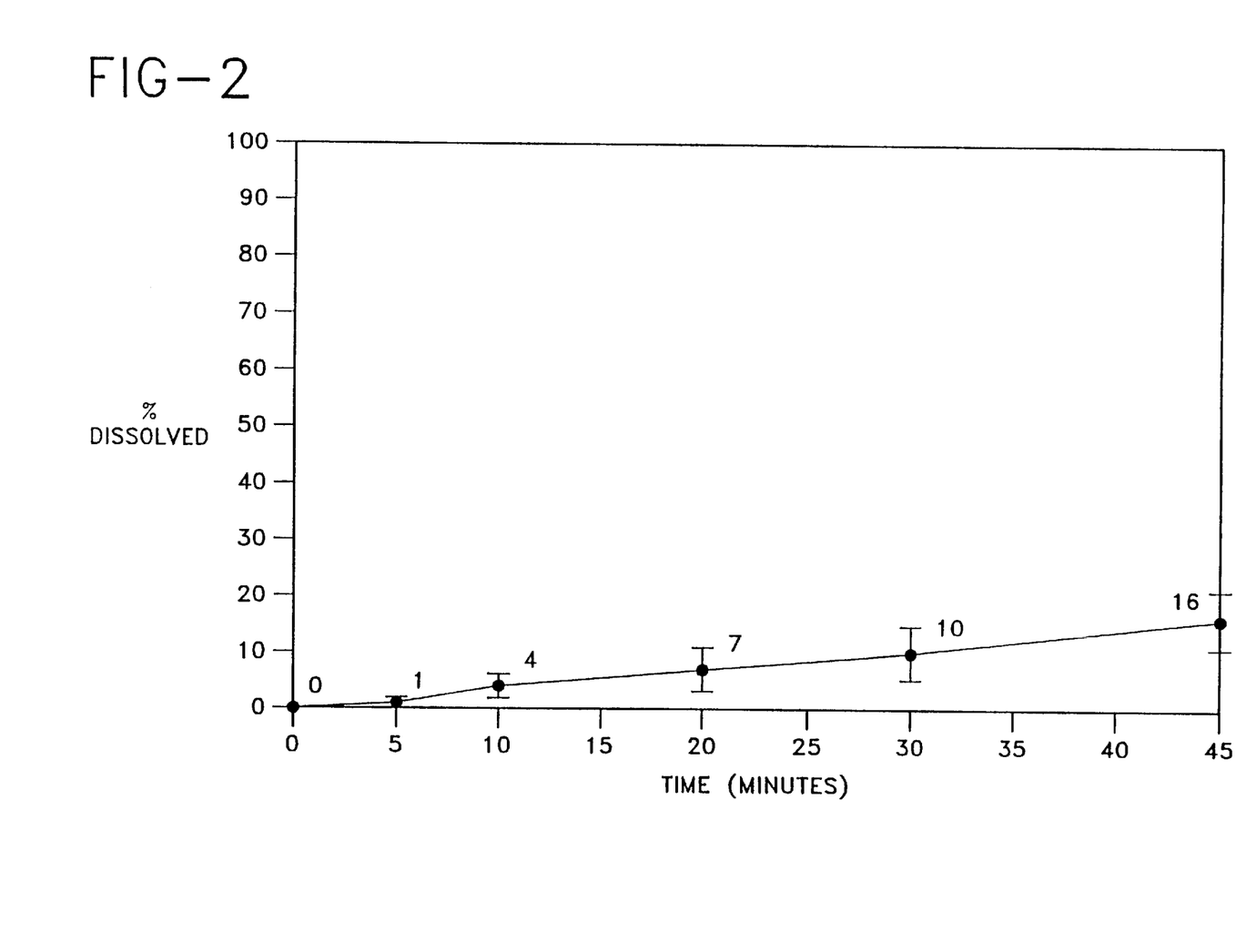

Dissolution testing of the material was performed using a simulated gastric fluid (no pepsin): 900 mL 0.1 N HCl, with 1% TWEEN 20, USP Method II. The sample was agitated, at 37° C., using 50 rpm for 30 min, and then using 200 rpm for 15 min. This solid dispersion was found to be 78% dissolved in 5 min, and 80% dissolved at 45 min. See FIG. 1. This compared to a meager 1% dissolution at 5 min, and no more than 16% dissolution at 45 min, when the bulk (raw) drug was tested. See FIG. 2.

Example 4
Extrusion-Mixing

The water-soluble polymer, EUDRAGIT E 100 was ground from pellet form to a fine powder and sized by passage through a 60 mesh sieve. The resulting sized powder was mixed with nifedipine and blended to form a blend including 20 wt % nifedipine in 80 wt % EUDRAGIT polymer.

The resulting powder blend was processed in an APV-Baker MP2015 twin screw extruder with multiple heater zones and fitted with a 1 cm nozzle. The temperature of each of the four heating zones was set to 175° C., and the following temperatures were recorded: Zone 1=172° C.; Zone 2=177° C.; Zone 3=175° C.; Zone 4=180° C. The speed of the twin screw was 120 rpm. The extruded product was a clear, yellow, solid dispersion of nifedipine in the polymethacrylate, having a discontinuous rod structure.

Figure 3:
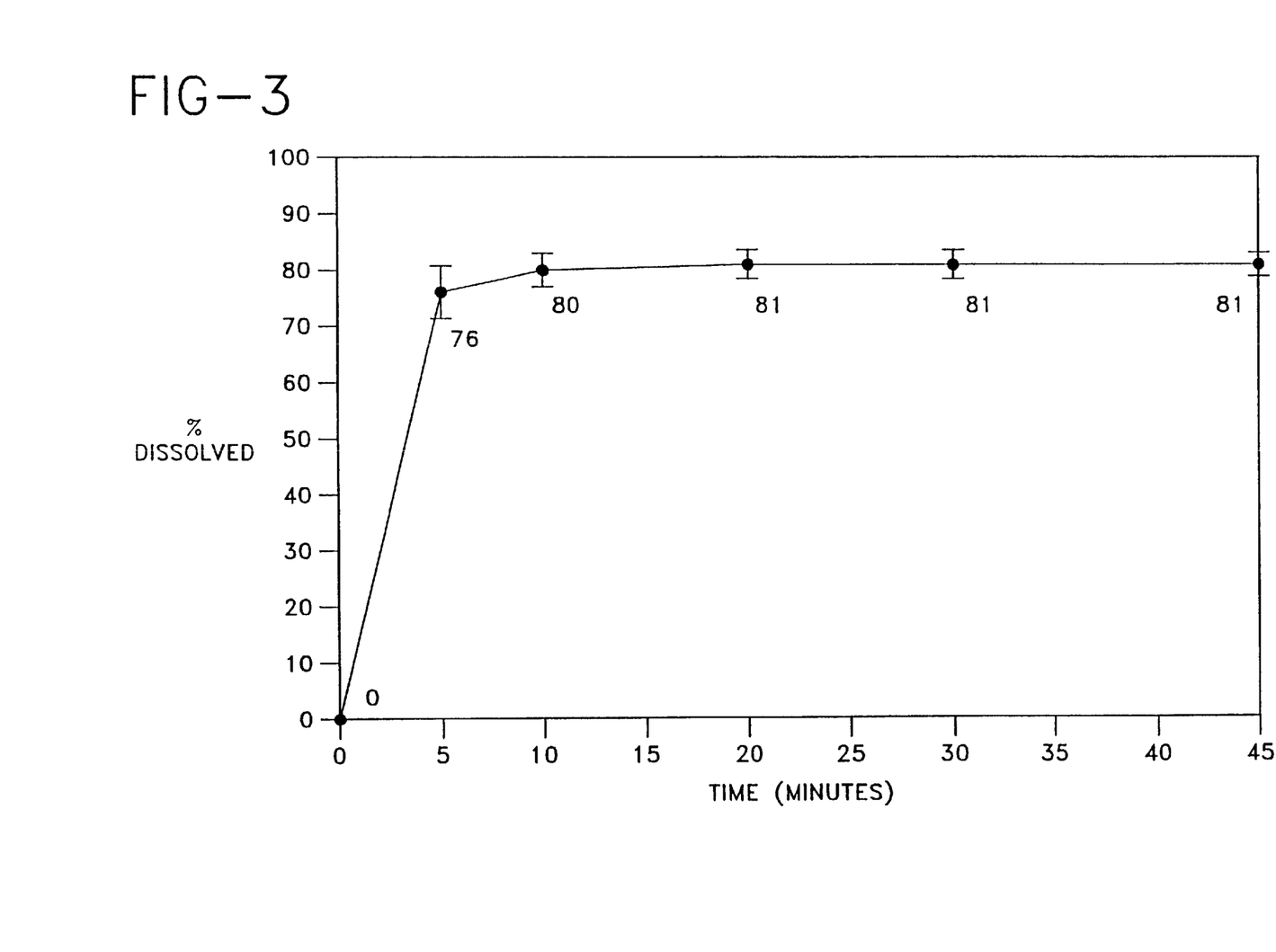

Dissolution testing of the extruded material was performed using a simulated gastric fluid (no pepsin): 900 mL 0.1 N HCl, with 1% TWEEN 20, USP Method II. The sample was agitated, at 37° C., using 50 rpm for 30 min, and then using 200 rpm for 15 min. This solid dispersion was found to be 76% dissolved in 5 min, and 81% dissolved at 45 min. See FIG. 3. This compared to a meager 1% dissolution at 5 min, and no more than 16% dissolution at 45 min, when the bulk (raw) drug was tested. See FIG. 2.

The present invention has been exemplified below in examples in which preparation of a substantially non-dissoluble bio-affecting agent, itraconazole, has been prepared in combination with a water-soluble polymer, Eudgragit®. Itraconazole is a potent anti-fungal drug. It has an aqueous solubility of less than 0.0001 g/mL of water. It was, therefore, selected as a model agent to demonstrate the capability of the present invention.

Figure 4:
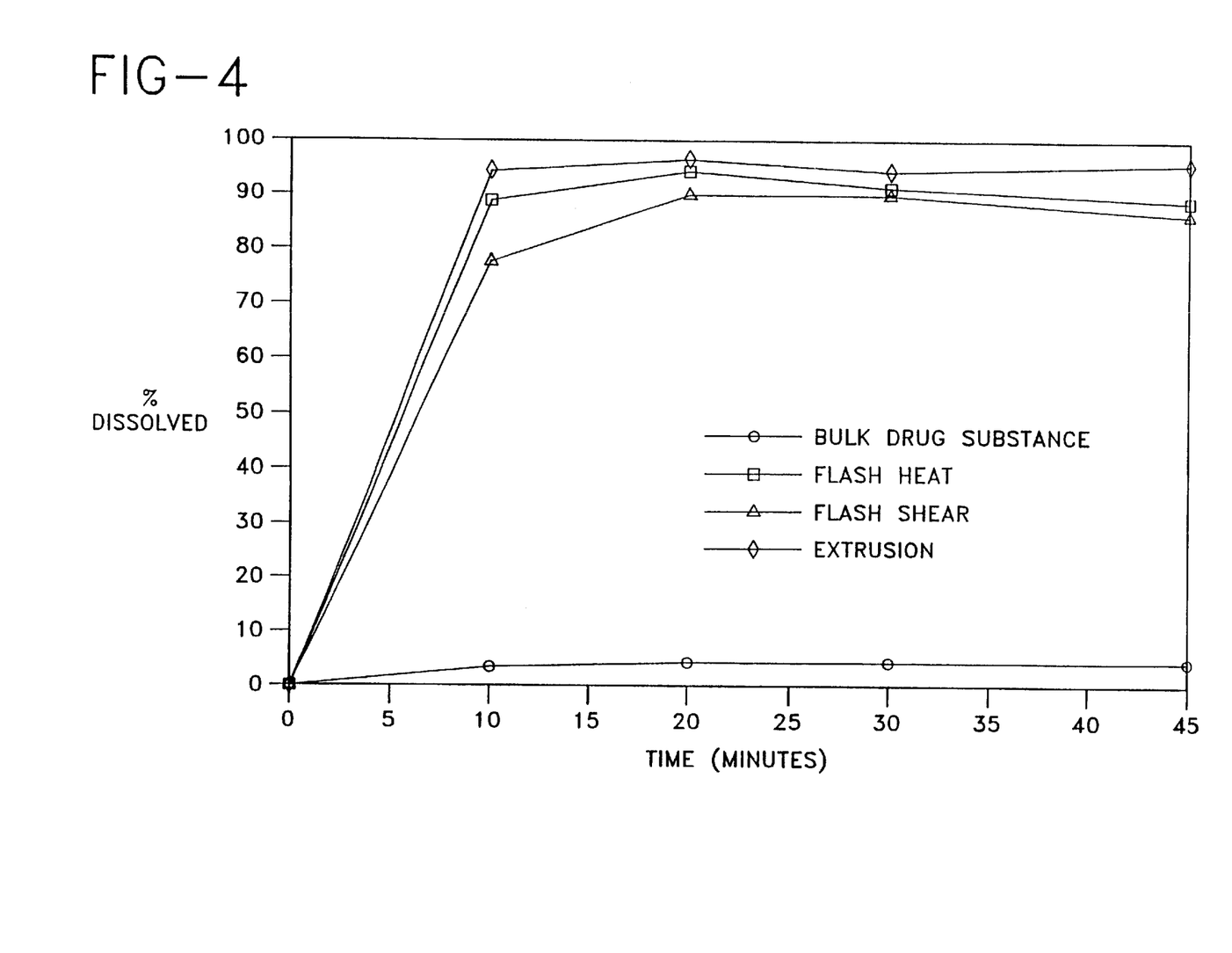

The comparative dissolution profiles have been illustrated in FIG. 4. The processed materials were examined microscopically during hydration in an acidic media, and showed the release of very fine nanocrystals of the drug from the fibers as the methacrylate dissolved. The extremely tiny size of these drug crystals as well as the rapid dissolution of the polymer allowed for rapid dissolution in vitro.

Example 5
Flash-Heat Process

In this example, the polymer EUDRAGIT E 100 (in pellet form) was ground to a powder and sized by passing the powder through a 60 mesh screen sieve. An antifungal agent was added to the resulting EUDRAGIT powder and blended together. The two ingredients were combined on a 1:1 ratio, i.e., the resulting blend had 50% itraconazole and 50% EUDRAGIT E polymer by weight.

The powder blend was processed in a spinning head operated at 60 Hz and 50% power cycling. Thus, the speed of the head was approximately 3,500–3,700 rpm and the temperature at the perimeter of the head was maintained at an average of approximately 218° C.

A fine clear floss was produced from the flash-heat process. Microscopic examination of the material in simulated gastric fluid (no pepsin) revealed the release of innumerable nanoparticles as the polymer solubilized. The size of the nanoparticles was not measurable by optical means and was well below 1 $\mu$m. It is believed that the size of the nanoparticles is of the order of 100 nm to 600 nm.

Dissolution testing of the material in simulated gastric fluid (no pepsin) 900 mL and 1% TWEEN 20, USP Method II, 100 rpm, gave 88% dissolution in 10 min. This compared to a meager 3.7% dissolution when the bulk drug substance was tested. See FIG. 4.

Example 6
Flash-Shear Process

Once again, the water-soluble polymer, EUDRAGIT E 100, was ground from pellet size to a fine powder and sized by passing the ground powder through a 60 mesh sieve. The resulting EUDRAGIT powder was mixed with the itraconazole and blended in a grinding mill. The powder blend was then processed in a flash-shear process using an extruder barrel temperature gradient from 164° C. to a 185° C. which a nozzle temperature of 185° C. and an atomization air pressure of 10 psi.

The Flash Shear nozzle at the exit end of extruder is of the type described in copending commonly-owned application Ser. No. 08/269,679, filed Sep. 6, 1994, where the air was heated to 170° C. and was at a pressure of 1.5 psi to 3 psi.

A thick fibrous material was produced by the process. Microscopic examination in simulated gastric fluid (no pepsin) revealed that a considerable number of nanoparticles were released from the water-soluble polymer as the polymer became solubilized. The size of the nanoparticles was well below 1 $\mu$m. It is believed that the size of the nanoparticles produced as a result of the present process is in the range of about 100 nm to about 600 nm. The material disappeared completely, with a milky dispersion remaining thereafter.

Dissolution testing of the material in simulated gastric fluid (no pepsin) of 950 mL and 1% Tween 20, USP Method II, 100 rpm, produced a 77% dissolution in only 10 min. Once again, this compared to a relatively low 3.7% dissolution when the bulk drug substance was tested. See FIG. 4.

Example 7
Extrusion Mixing

The water-soluble polymer, EUDRAGIT E 100 was ground from pellet form to a fine powder and sized by passage through a 60 mesh sieve. The resulting sized powder was mixed with the itraconazole at a ratio of 1:1 and blended in a grinding mill.

The resulting powder blend was processed in a twin screw extruder fitted with a 1 cm nozzle. A clear extrudate was produced by the process. The appearance of the material quickly turned to an opaque, hard, and brittle rope. Microscopic examination of the resulting extrudate in simulated gastric fluid (no pepsin) revealed the release of a considerable number of very fine particles, having a size of well below 1 $\mu$m. The extrudate disappeared completely with a milky dispersion remaining thereafter.

Dissolution testing of the material in simulated gastric fluid (no pepsin) of 900 mL and 1% Tween 20, USP Method II, 100 rpm, produced a 94% dissolution in 10 min. This compared to only 3.7% dissolution when the bulk drug substance was tested. See FIG. 4.

Example 8
Capsule Formulation

Ten grams (10 g) of the 50/50 antifungal/EUDRAGIT E solid dispersion of Example 7 was ground using a rotary blade, and then sieved through a 20 mesh screen. We were able to load 400 mg of the solid dispersion in a 0 size capsule, to give a capsule containing 200 mg of the antifungal agent. The material was free flowing, having all of the properties of an ideal material for capsule filling.

Example 9
Tablet Formulation

The acid-soluble polymer, EUDRAGIT E 100 was ground from pellet form to a fine powder and sized by passage through a U.S. Standard 60 mesh sieve. The resulting powder was mixed with the antifungal agent at a ratio of 1:1 and blended in a grinding mill.

The powder blend was processed in a twin screw extruder fitted with a 1 cm nozzle. This extrudate was cooled and the material was ground in a high shear grinding mill to reduce particle size. Microcrystalline cellulose NF(AVICEL PH101) and croscarmellose sodium NF were blended with the solid dispersion to provide 15.0% and 3.00% of the blend, respectively. The antifungal agent and EUDRAGIT E each were 41% of the blend.

The tablet premix was compressed on a Specac hydraulic press at 13,000 psi using an 11 mm tablet die, to give 236 milligram tablets. These tablets provided a target dose of 100 mg of the antifungal agent. The tablet had a disintegration time of 13 min in simulated gastric fluid (no pepsin) at 37° C.

Example 10
Particle Size Distribution

A sample of a solid dispersion of the antifungal agent prepared by flash heat processing according to Example 6 above was subjected to particle sizing. Two hundred milligrams (200 mg) of the solid dispersion was dissolved in 900 mg of 0.1 N HCl. After 9 min, an aliquot was removed and tested using a standard photon correlation method. Computerized analysis indicated that the mean particle size in the sample was 196.8 nm, with a monomodal distribution of particle sizes of from about 155 nm to about 255 nm. These particles clearly qualify as "nanoparticles" as described hereinabove.

The compositions of all of the examples can be easily be molded into tablets by using opposed roller dies or regular dies following the co-processing (flash flow or co-extrusion) steps. Experience shows the material is readily compressible into tablets of pressures of less than 80,000 psi and preferably of pressures of from about 500 psi to about 40,000 psi.

The foregoing examples make it abundantly clear that dissolution of the solid dispersions of the invention in an aqueous environments is very efficient. Moreover, tablets or capsules made according to the invention provide very convenient delivery of substantially non-dissoluble bio-affecting agents. Accordingly, the composition and method of the invention advantageously improve the bio-availability of substantially non-dissoluble bio-affecting agents.

Thus, Applicants have described what are presently believed to be the preferred embodiments of the present invention, and other and further embodiments of the invention will be appreciated by those skilled in the art, and it is intended to include other modifications and changes which come within the true scope of the invention as pointed out in the appended claims.

What is claimed is:

1. A composition for delivery of a substantially water-insoluble bio-affecting agent to a bio-system, comprising:
   a solid substantially uniform dispersion of said bio-affecting agent and a water-soluble polymer, said water-soluble polymer comprising a terpolymer of butyl(meth)acrylate, (2-dimethyl aminoethyl)(meth)acrylate, and methyl(meth)acrylate in relative proportions of 1:2:1 and wherein said water-soluble polymer is compatible with said bio-affecting agent and wherein said bio-affecting agent is fixed in an increased-energy state by said polymer, whereby said agent is released in solution in the form of nanoparticulates.

2. The composition of claim 1 wherein the process used to combine the bio-affecting agent and the polymer is selected from the group consisting of flash flow and extrusion processing.

3. The composition of claim 2, wherein the water-soluble polymer is soluble in aqueous media having an acid pH.

4. The composition of claim 2 made via flash flow processing.

5. The composition of claim 2 made via extrusion mixing.

6. The composition of claim 1, wherein said bio-affecting agent is selected from the group consisting of: antifungals, anti-inflammatories, anti-hypertensives, antimicrobials, steroidal drugs, hormones, prostaglandins, interferons, and mixtures thereof.

7. The composition of claim 6, wherein the bio-affecting agent is selected from the group consisting of: antifungal, anti-inflammatory and anti-hypertensive agents.

8. The composition of claim 6 wherein said antifungal is selected from the group consisting of itraconazole and griseofulvin.

9. The composition of claim 8 wherein said antifungal itraconazole.

10. A dosage unit made from the composition of claim 1.

11. A method of enhancing the solubility of a substantially water-insoluble bio-affecting agent in an aqueous environment of a bio-system comprising:
    transforming said agent into a {molecular} solid substantially uniform dispersion with a water-soluble polymer, said water-soluble polymer comprising a terpolymer of butyl(meth)acrylate, (2-dimethyl aminoethyl)(meth)acrylate, and methyl(meth)acrylate in relative proportions of 1:2:1, wherein the solid dispersion is formed via a process that uses one or more flash flow or extrusion mixing techniques and wherein said bio-affecting agent is fixed in an increased-energy state by said polymer.

12. The method of claim 11 wherein the process used to combine the bio-affecting agent and the polymer is a continous one.

13. The method of claim 12, wherein said processing is flash flow processing.

14. The method of claim 12, wherein said processing is extrusion mixing.

15. The method of claim 11, wherein said water-soluble polymer is soluble in aqueous media having acid pH.

16. The method of claim 11, wherein said agent is selected from the group consisting of: antifungals, anti-inflammatories, anti-hypertensives, antimicrobials, steroidal drugs, hormones, prostaglandins, interferons, and mixtures thereof.

17. The method of claim 16 wherein said antifungal is selected from the group consisting of itraconazole and griseofulvin.

18. The method of claim 17 wherein said antifungal is itraconazole.

19. The method of claim 11, wherein the bio-affecting agent is selected from the group consisting of: antifungal, anti-inflammatory and anti-hypertensive agents.

20. The method of claim 11 further including the step of processing into one or more dosage units.

21. A dosage unit made by the method of claim 20.

22. A method for delivering a bio-affecting agent to a bio-system, comprising:
    administering to said bio-system a solid substantially uniform dispersion comprising said bio-affecting agent fixed in an increased-energy state in a water-soluble polymer, said water-soluble polymer comprising a terpolymer of butyl(meth)acrylate, (2-dimethyl aminoethyl)(meth)acrylate, and methyl(meth)acrylate in relative proportions of 1:2:1, wherein said solid dispersion renders said bio-affecting agent bio-available to said bio-system in the form of nanoparticulates having enhanced solubility.

* * * * *